(12) United States Patent
Kilper

(10) Patent No.: US 8,268,265 B2
(45) Date of Patent: Sep. 18, 2012

(54) APPARATUS AND METHOD FOR PICKING UP, TRANSPORTING, AND DEPOSITING MICROSCOPIC SAMPLES

(75) Inventor: Roland Kilper, Jena (DE)

(73) Assignee: Roland Kilper, Jena (DE)

( * ) Notice: Subject to any disclaimer, the term of this patent is extended or adjusted under 35 U.S.C. 154(b) by 602 days.

(21) Appl. No.: 12/440,679

(22) PCT Filed: Jul. 4, 2007

(86) PCT No.: PCT/EP2007/005899
§ 371 (c)(1),
(2), (4) Date: Mar. 10, 2009

(87) PCT Pub. No.: WO2008/037305
PCT Pub. Date: Apr. 3, 2008

(65) Prior Publication Data
US 2009/0252590 A1 Oct. 8, 2009

(30) Foreign Application Priority Data
Sep. 25, 2006 (DE) .......................... 10 2006 045 620

(51) Int. Cl.
*A61B 10/00* (2006.01)

(52) U.S. Cl. .......... 422/536; 422/50; 422/500; 422/501; 257/414; 436/180

(58) Field of Classification Search .................. 422/536, 422/50, 500–501; 257/414; 436/180
See application file for complete search history.

(56) References Cited

U.S. PATENT DOCUMENTS

| | | | |
|---|---|---|---|
| 5,348,883 A | 9/1994 | Togawa | |
| 6,669,906 B1 | 12/2003 | Schalkhammer et al. | |
| 6,673,086 B1 | 1/2004 | Hofmeier et al. | |
| 6,783,734 B1 | 8/2004 | Goldstein et al. | |
| 6,943,417 B2 * | 9/2005 | Boland et al. | 257/414 |
| 7,393,629 B2 | 7/2008 | Fuhr et al. | |
| 2003/0032082 A1 | 2/2003 | Leclerc | |
| 2009/0045354 A1 | 2/2009 | Sagmuller et al. | |

FOREIGN PATENT DOCUMENTS

| | | |
|---|---|---|
| DE | 692 10 753 T2 | 10/1996 |
| DE | 198 04 800 A1 | 8/1999 |
| DE | 199 32 032 C2 | 2/2001 |
| DE | 298 12 625 T2 | 3/2004 |
| DE | 10 2005 026 540 A1 | 12/2006 |
| EP | 0 539 888 A1 | 5/1993 |

(Continued)

*Primary Examiner* — Jyoti Nagpaul
(74) *Attorney, Agent, or Firm* — Patterson Thuente Christensen Pedersen, P.A.

(57) ABSTRACT

An apparatus and method for picking up, transporting and depositing microscopic samples. Such an apparatus includes at least one interchangeable adhesive body and a gripping tool for picking up, transporting and depositing the adhesive body, the adhesive body having at least one outwardly curved surface which is at least partially adhesive with respect to the sample. In this method, a gripping tool picks up an adhesive body having an at least partially outwardly curved surface which is at least partially adhesive with respect to the sample. The gripping tool then guides the adhesive body to above the sample. The at least partially curved surface of the adhesive body is then brought into contact with the sample, the sample adheres to the surface of the adhesive body when this is being removed from the sample location, and is finally deposited at the depositing location.

8 Claims, 4 Drawing Sheets

FOREIGN PATENT DOCUMENTS

| | | |
|---|---|---|
| EP | 0 979 408 B1 | 10/2004 |
| EP | 1 250 583 B1 | 7/2006 |
| JP | 2002-503345 A | 1/2002 |
| JP | 2005-210931 A | 8/2005 |
| WO | WO 97/13838 | 4/1997 |
| WO | WO 98 35215 | 8/1998 |
| WO | WO 98 36261 | 8/1998 |
| WO | WO 99/00658 | 1/1999 |
| WO | WO 02/12896 A1 | 2/2002 |
| WO | WO 03/047738 A2 | 6/2003 |
| WO | WO 03/048786 C2 | 6/2003 |
| WO | WO 03/107066 A1 | 12/2003 |
| WO | WO 2004/046734 A1 | 6/2004 |
| WO | WO 2004/074424 A2 | 9/2004 |
| WO | WO 2004/074426 A2 | 9/2004 |
| WO | WO 2005/033668 A1 | 4/2005 |
| WO | WO 2005/123227 A2 | 12/2005 |
| WO | WO 2007/054161 A1 | 5/2007 |

\* cited by examiner

APPARATUS AND METHOD FOR PICKING UP, TRANSPORTING, AND DEPOSITING MICROSCOPIC SAMPLES

PRIORITY CLAIM

The present application is a National Phase entry of PCT Application No. PCT/EP2007/005899, filed Jul. 4, 2007, which claims priority from German Application Number 102006045620.0, filed Sep. 25, 2006, the disclosures of which are hereby incorporated by reference herein in their entirety.

FIELD OF THE INVENTION

The invention relates to an apparatus and a method for picking up, transporting and depositing—collectively referred to as transferring—microscopic samples.

BACKGROUND OF THE INVENTION

In biological and biomedical research as well as in forensic investigations, very small quantities of biological material have to be isolated at a sample location, transported from the sample location to a depositing location and subsequently analyzed. The samples are frequently taken from laboratory preparations such as tissue sections, which may, for example, rest on specimen slides suitable for microscopy. Especially in forensic examinations, a sample frequently has to be picked up from irregular or opaque surfaces as, e.g., from parts of some piece of clothing or a cigarette butt. Such samples have to be picked up from a definite spot as accurately as possible, i.e. a particular sample must be selected and isolated out of many samples situated at close spaces. This sample must then be taken to a depositing location without getting contaminated; ideally, this process is documented or at least monitored. The samples must be deposited at a depositing location—for example, an Eppendorf vessel or a biochip—as accurately as possible as required by the depositing location or vessel.

There are several approaches in prior art to solving the said problem, none of which is satisfactory. Many pick-up techniques have been developed in connection with microdissection by means of laser beams. Before taking the sample, a laser beam is used to cut out pieces from tissue placed on a specimen slide. Most of the techniques developed for taking up the cut-out tissue are based on the application of layers of adhesive film.

For example, WO 97/13838A1 describes a selectively activable transfer surface: The tissue section on a specimen slide is covered with a transparent transfer film, which itself is attached to a slide. The transfer film is a polymer having thermoplastic properties, i.e. it fuses when heat is applied to it. By means of infrared laser irradiation, the film can be stuck with pinpoint accuracy to the bits of tissue to be isolated, so that after microdissection, when the film together with the slide is lifted off the sample, only these bits of tissue adhere to it. The sample bits cut out can then be deposited in a reaction vessel either with or without the transfer film.

A similar approach is followed in WO98/36261A1 and WO 98/35215A1. Here, a multilayer transfer film is described, which also has thermoplastic properties and contains at least one metal film and a supporting layer. This film is mounted on a carrier, this carrier being shaped as the lid of an Eppendorf vessel. The lid with the film is brought into contact with the sample; laser treatment makes the sample bits of interest adhere to the lid. After the microdissected material has been lifted off, the lid can be placed on the Eppendorf vessel, thus closing the vessel, and the sample can be brought into contact with a reaction solution.

EP 1 250 583 B1 describes a method in which the sample is covered with a foil. The pick-up tool, a carrier with an adhesive coat, is placed on the foil. Subsequently the sample portions of interest are isolated by means of laser microdissection, with the laser severing the tissue and the foil. In this way, only the material cut out adheres to the carrier when the pick-up tool is lifted off the sample surface. Here again, the carrier is preferably shaped as the lid of an Eppendorf vessel; alternatively, a piece of adhesive tape can be used.

Another solution is described in EP 0 879 408 B1. Here again, microdissection is performed at first. By a laser pulse, the microdissected material is then released from the specimen slide and ejected up, where it hits the lid of an Eppendorf vessel. Preferably, the lid has an adhesive coat, so that the material sticks to the lid. Alternatively, an adhesive disc of foil may be used as the capturing surface, which is then placed into an Eppendorf vessel.

The solution approaches described above have several disadvantages, though. Assembly of the carrier layers for the adhesive material is laborious; moreover, the methods necessitate the use of a laser, either for microdissection and simultaneous activation of the adhesive properties of the carrier material, or for subsequent ejection of the dissected material from the specimen slide onto an appropriate carrier. In forensic examinations, for example, the application of such methods is limited, as the sample carriers used there do not readily allow microdissection. Also, ejecting an object from the sample is a step that involves a certain inaccuracy, whereas in forensic examinations, in particular, it must be ensured that actually the desired sample bit has been taken. In addition, as inverse microscopes are used for laser microdissection, the capability of documentation and monitoring is greatly restricted. Exact deposition of the objects at the depositing location intended for them is not guaranteed. In addition, if the samples are very small, e.g. if they are single cells only, the methods described above, in which the isolated material is taken up in an Eppendorf lid, cannot be used, as the volume of the reaction liquid is so small as to make safe detachment of the cell from the lid unlikely, so that, in the subsequent analysis, the necessary chain reaction for amplifying the material cannot be released.

In other methods known in prior art, various tools are used instead of carrier films or the like, for taking up the isolated material.

In WO 97/13838A1, an adhesive tip is described with which bits of tissue can be taken up from specimen slides. The tip is dipped into a mixture of a commercial polyterpene-based resin and xylene. This solution is used as an adhesive. The sample is then taken up with the tip and adheres to the resin-xylene mix. The material taken up is transferred to an analytical vessel. This vessel contains a reaction solution, which cancels the adhesive action of the tip or the resin-xylene mix. The material taken up thus detaches from the tip and remains in the solution. For the next application the tip is again dipped into the adhesive solution. As this is still the same tip, freedom from contamination is not guaranteed.

The procedure described in WO 97/13838 suffers from the same disadvantage. Here, a sharp-edged glass pipette is described, with which bits of tissue can be dug out, which can then be held to the inlet of the capillary by suction. If the suction ceases, the sample can be deposited. It is a disadvantage, though, that especially very small samples—such as single cells—will easily remain stuck to the capillary and fail to detach from it when the suction ceases. Here again, freedom from contamination is not guaranteed.

EP 0 539 888 B1 describes a selecting apparatus for cell clusters and for cells enclosed in gel granules. The apparatus comprises, among other items, a capillary for taking up the objects. This capillary is dipped into a starch-like adhesive, which makes the cell stick to the tip of the capillary. For depositing the cell, the capillary with the cell adhering to it is moved to above a capturing vessel containing a liquid. By means of compressed air blown through the capillary, the adhesive and the cell detach from the tip and drop into the liquid. Apart from the circumstance that the method is suitable only for larger samples, the depositing process cannot be reproduced, so that it is difficult to document, and, moreover, incapable of precisely positioning the cell clusters. In addition, when the cell is blown off, adhesive is blown off with it, which may cover the cell, thus making analysis difficult if not impossible.

DE 198 04 800 A1 describes a solution in which a needle is used as the transfer tool. Picking up and depositing are assisted by suction or pressure, electrostatic or magnetic interactions. WO 97/13838 also describes a needle to which biological material sticks because of electrostatic interaction. An essential disadvantage of using a needle as transfer tool is that the cell, when being released from the needle, cannot be precisely positioned. This disadvantage is detrimental especially if Eppendorf vessels are used, where pin-point accuracy in positioning the object onto the single-drop quantity of reaction liquid is important. If, e.g., the cell is dropped into an Eppendorf vessel by switching off the magnetic action, it is quite possible for the cell to stick to the wall of the vessel rather than getting into contact with the reaction liquid, and thus fail to be analyzed. Also, due to the electrostatic forces, unwanted picking-up of further material cannot be excluded. The probability for this to happen is high especially if—as in forensic examinations—samples are picked up from, e.g., articles of clothing consisting of synthetic fibers, which easily become electrostatically charged.

WO 2005/033668 A1 describes another microdissection method, in which the tissue cut out is fixed to the specimen slide electrostatically. The tissue cut out can then be picked up electrostatically by means of an electrode or sucked to a relatively broad contact surface measuring about 500 µm in diameter and provided with air channels. The air channels have diameters of 8 µm only. The tissue section is then deposited on a sticky substrate. As in case of the needles described above, the transfer of smallest biological objects, such as single cells, by means of an electrode cannot be reproduced. If, on the other hand, the contact surface is used, the large diameter of that surface makes depositing with pin-point accuracy impossible. The large dimension of the contact surface further bears the risk of contamination.

Finally, WO 2004/046734 A1 describes an apparatus for harvesting cells and cell colonies from liquid cultures and semisolid media. A cell is sucked in through a glass capillary. A robot arm then moves the glass capillary to a suitable analysis carrier, e.g. a microtitration plate, where the cell is deposited. Intended for high sample throughputs, the method described in WO 2004/046734 A1 is ill-suited for the investigation of single samples. Also, this method requires a liquid as a taking-up and depositing medium.

SUMMARY OF THE INVENTION

It is the problem of the invention, therefore, to develop an apparatus and a method permitting samples having the size of a cell to be picked up from a wide variety of carrier materials and subsequently to be deposited at a location intended therefor with the greatest possible exactitude, and without contamination in transit. Preferably, it should be possible to document the picking-up, transporting and depositing of the sample.

The problem is solved by an apparatus for picking up, transporting and depositing microscopic samples, that comprises at least one interchangeable adhesive body and a gripping tool for picking up, transporting and depositing the adhesive body, wherein the adhesive body has at least one outwardly curved surface that is at least partially adhesive with respect to the sample. Gripping tool and adhesive body, then, are two separate components, with the gripping tool picking up the adhesive body.

Apart from the curved surface, the adhesive body may have any form. By means of the outwardly curved surface of the adhesive body, it is possible to selectively pick up smallest quantities of biological material of the size of a cell. The curved surface is at least partially made adhesive with respect to the sample. The kind of adhesion may be varied from sample to sample; for example, differently coated adhesive bodies may be provided, one of which is selected as appropriate for the sample, either by the gripping tool or an operator handling the gripping tool. The adhesive feature of the surface may be restricted to a very small area. In this way, the certainty that only the desired sample bit is picked up can be increased. However, the adhesive body or its curved surface may also be made adhesive over its entire surface.

In one embodiment, the adhesive surface of the adhesive body is designed in such a way that a single cell, but not a larger aggregate of cells, will adhere to it and can easily be detached from that surface. The adhesive body is interchangeable, i.e. for taking the next sample, the adhesive body used before is replaced with a new one, so that samples are always picked up without contamination. As the area where the curved surface makes contact with the sample at a particular sample location is very small, not only the picking-up but also the depositing of the sample is possible with pin-point accuracy, provided the degree of curvature of the surface is high enough. It is also possible to use plane surfaces instead of curved ones, but this will not permit high-accuracy targeting in picking up and depositing if the surface is too large. If the plane surface is small enough, it can be used as an equivalent, but adhesive bodies with curved surfaces are easier to make and to use, as they can have larger dimensions. Finally, it is even possible to use inwardly curved surfaces. With a slight curvature, the effect is similar to that of a plane surface; with stronger curvatures, contact will—contrary to the outwardly curved surface—predominantly be made at the rim, if the surface corresponds, for example, to an introverted membrane.

In one embodiment, the gripping tool is designed as a pair of tweezers. The tweezers may also be designed as inverted tweezers, in which the two legs are closed when not pressed. Also, the tweezers may be made of a single part, with an elastic hinge making the legs movable.

The gripping tool may be made interchangeable; in this way it is possible, for example, to use different types of tweezers to match the sizes of different adhesive bodies. This also allows the use of tweezers made of different materials. For executing the gripping function, i.e., in case of tweezers, for opening and closing the legs, it is expedient for the gripping tool to have a gripping mechanism, which may be driven, e.g., piezoelectrically, electromechanically, magnetically or pneumatically. Other kinds of drive are also feasible, as far as they are capable of providing the tiny positioning increments required.

In one embodiment, the gripping tool is at least partially coated with a layer of fluorescent material. This permits, for example, the picking up of a fluorescent sample, or one provided with fluorescent markers, without the influence of interfering ambient light. Varying with the sample, different gripping tools may be used which are provided with coatings that fluoresce at different frequencies and can be interchanged as necessary.

In another embodiment, the adhesive body is designed as a sphere, with the sphere preferably having a diameter between 10 μm and 500 μm. Then, the surface can be made adhesive throughout. The advantage of spheres is that their form permits smallest contact areas. Moreover, they are easy to manufacture and to store. Furthermore, if the complete sphere is provided with an adhesive surface, the sphere can be taken up by the gripping tool at random, which simplifies its handling. Of course, many other shapes are also suitable for the adhesive body, for example lenses, ellipsoids, cylindrical bodies with rounded top and/or bottom surfaces.

The adhesive body, too, may consist of fluorescent material or at least be provided with a coating of some fluorescent material, so that it enables the picking-up of material selected for its fluorescence.

In one embodiment, the adhesive bodies are at least partially made of plastics, preferably of polystyrene. Alternatively, they may be made of cellulose or some cellulose derivative. Manufacturing such spheres is possible at particularly low cost, and besides, these materials are inactive with regard to reactions with the biological materials commonly to be picked up. Alternatively, the adhesive bodies may consist at least partially of some magnetic or at least magnetizable material. This can be of advantage, e.g., if the sphere is deposited on a magnetized surface. This may either be a depositing location where the sample is prepared for the subsequent analysis, or, after the sample has been deposited, a container in which the adhesive bodies used are collected for subsequent cleaning. It is not necessary that the entire adhesive body consists of magnetic material; it is sufficient if it has a core of magnetic or magnetizable material. It must be guaranteed, though, that magnetic interaction is possible between the surface on which the adhesive body is deposited and the core of the adhesive body. Another alternative is coating the surface with a magnetic or magnetizable material. Other materials are also feasible; for example, it may make sense to use glass spheres, as a sample adhering to a glass sphere is particularly easy to deposit into water.

In an embodiment of the invention, the at least one curved surface of the adhesive body is at least partially provided with an adhesive coat of some polypeptide or polymer. For example, biosynthetic polypeptides of non-animal origin or cellulose derivatives may be used. Such a coating has the great advantage that the coat has no adhesive action whatsoever with regard to common surfaces such as metal, glass etc., as those of a specimen slide or of the gripping tool; i.e., the adhesive action is selective in that it is restricted to biological samples, especially to cells. This considerably facilitates the handling of the combination of gripping tool and adhesive body. All other coatings exhibiting such selective adhesive action are also suitable and can be regarded as equivalents. In addition, the adhesive body may have the properties of hydrogels and may be liquefied, at least locally, preferably by the action of heat and/or force, which may facilitate the picking up of cells.

As the adhesive bodies are contaminated after one-time use, a new adhesive body has to be used for every sample transfer (this comprises the picking up, transport and deposition of the sample). Therefore, it is expedient for the apparatus to be provided with a reservoir with a great number of adhesive bodies. A new adhesive body can then be fetched from the reservoir with the gripping tool. In the simplest case, the reservoir is a tray. Preferably, however, the reservoir is provided with a dispenser for dispensing one adhesive body at a time. In this way it is also possible to automate the taking up of the adhesive body from the dispenser, if the gripping tool is guided by a suitable control device, because in this case the location at which an adhesive body is taken up is always the same.

For observing the picking up, transport and, where appropriate, deposition of the sample, the apparatus is preferably provided with a microscope, preferably a stereomicroscope. This permits the process to be monitored continuously.

In another particularly preferred embodiment of the invention, the apparatus is provided with a micromanipulator for handling the gripping tool. Such a micromanipulator has a holder in which the gripping tool is fixed and thus joined to the micromanipulator. Optimally, such a micromanipulator is movable in all three spatial directions, so that the gripping tool can be moved to anywhere within a defined volume. If the apparatus is also provided with a microscope, it makes sense to arrange the micromanipulator right next to it, so that the gripping tool with the adhesive body can be moved into the image field of the microscope. In one embodiment, the micromanipulator is connected with a control device, so that manual control is possible, e.g. by means of a joystick, in order to move the gripping tool with the adhesive body to above the sample, pick up the sample and transport it to the depositing location. This process may also be partly automated, if the spatial position of the adhesive body relative to the depositing location is known. The position can be determined, e.g., by means of a position measuring device as described in DE 10 2005 053 669.7. After the sample has been picked up, transport to the depositing location—e.g. a biochip that is arranged at a location designed therefor and whose coordinates are known—can be performed automatically. If the sample is deposited without the adhesive body, depositing the used adhesive body and taking up a new adhesive body can also be performed automatically.

In another embodiment of the invention, means for generating a microvibration in the gripping tool are provided. If the gripping tool is, for example, held by a micromanipulator, the microvibration can be generated in the manipulator. This can, for example, be made to vibrate with amplitudes of a few micrometers, e.g., piezoelectrically or by means of other suitable driving devices. The driving device may also be arranged inside the manipulator itself, so that only the gripping tool is made to vibrate. Finally, the gripping tool itself may be designed to have a suitable piezoelectrical, electromotive or other mechanism for generating vibrations. If the gripping tool is a pair of tweezers, the said mechanism may be arranged, e.g., between the two legs and make them vibrate in parallel, so that the ends of the tweezers are deflected from their rest positions in parallel.

If a microvibration is generated in the gripping tool, this will in some cases facilitate the picking up of the sample: When the adhesive body gets into contact with the sample, the sample sticks to it. As a rule, however, the sample at the same time also sticks to the surface from which it is to be removed, so that it may be difficult to release from the latter or even get damaged when the gripping tool with the adhesive body and the sample adhering to it are removed, because, especially in case of a single cell, the tensile force applied may be excessive so that the cell gets torn. If, however, a microvibration of the gripping tool can be activated in addition, this will help to reduce sample adhesion to the surface from which the sample is to be picked up.

In addition, it is preferable to provide the apparatus with means to generate an impact amplitude in the gripping tool. This is helpful especially in depositing, where it facilitates depositing the adhesive body—with or without sample—at a location designed for it, because the adhesive body may tend to remain stuck to the gripping tool. This impact amplitude may be generated, e.g., with a little hammer operating on a piezoelectrical basis. The little hammer may, e.g., be integrated in the micromanipulator or in the gripping tool itself.

In another embodiment of the invention, means are provided for at least partially monitoring the picking up, transporting and/or depositing the sample. In the simplest case, the transfer may be observed through the microscope. An observer, e.g. a certified expert, can then confirm that a sample has indeed been picked up and deposited in the respective place. Advisably, though, the means for monitoring comprise a camera. Such a camera allows the entire transfer process, i.e. from picking up the sample up to its depositing, to be documented and monitored either continuously or at intervals. The camera may, for example, be connected to a separate output port in the tube; this is preferable especially if the picking up of the sample is to be monitored. The camera may also be arranged externally. In this way it is possible to monitor and document also the deposition of the sample in the depositing location, which, as a rule, is outside the image field of the microscope. If the light reaches the camera via a port in the tube, the camera can be employed, in particular, to automatically select the sample to be picked up, using suitable image processing algorithms. By means of a suitable control device controlling the gripping tool guided by a micromanipulator, the entire transfer process can then pass off automatically. Naturally, the micromanipulator has the capability to open and close the gripping tool, i.e. to execute the gripping function. Preferably, the control of the micromanipulator is designed in such a way that—in case of automatic guiding or manual guiding, e.g. with the aid of a joystick—the speed with which the manipulator moves through the image field observable in the microscope or the camera depends on the magnification selected on the microscope. Thus, the drive of the micromanipulator is controlled depending on the magnification chosen. Preferably, this dependence is selected in such a way that the manipulator is moved at a higher speed with a low magnification, and at a slower speed with a high magnification. In another embodiment, the speed observed in the image field is independent of the selected microscope magnification.

For documenting and monitoring the transfer it is furthermore of advantage if the gripping tool is made rotatable at least about its longitudinal axis, so that the adhesive body with the sample adhering to it can be rotated into the direction of the observer or the camera. This may serve to check whether the sample has actually been picked up, but also to document that the sample picked up is really the one previously selected. The rotation may also be executed by the manipulator, which may be provided with a suitable rotating mechanism. If a sample is picked up, it is at first fixed to the bottom side of the adhesive body, which faces the surface from which the sample is removed, a location out of sight of an observer viewing the operation through an upright stereomicroscope. By the rotation of the gripping tool, the bottom side is turned into the visual field of the observer, who can now see whether a sample actually adheres to the adhesive body. With a camera accessed via the tube, the entire operation can be documented. If the camera is attached below the sample carrier and if this is transparent, the rotation is not required. By means of the micromanipulator the sample can be moved to a location where a camera is installed.

In addition, the means for monitoring may also comprise at least one mirror; the adhesive body with the sample sticking to it can then be imaged into the direction of an observer or the camera via the at least one mirror. Here again, rotation may be unnecessary, depending on where the mirrors and the camera are arranged relative to the surface from which the sample is removed.

The problem is also solved by a method for transferring a microscopic sample from a sample location to a depositing location, in which a gripping tool picks up an adhesive body with an at least partially curved surface that is at least partially adhesive with respect to the sample, and in which the gripping tool guides the adhesive body to above the sample, and in which the at least partially curved surface of the adhesive body is made to contact the sample, and in which the sample adheres to the surface of the adhesive body when the latter is removed from the sample location, and in which the sample is deposited at the depositing location. These process steps can be carried out especially with an apparatus according to the invention, as described above.

At first, then, a gripping tool, e.g., a pair of tweezers, picks up an adhesive body with an at least partially curved surface. The adhesive body may be configured, e.g., as a sphere. The partially curved surface is designed to be at least partially adhesive with respect to the sample. The gripping tool, which may be guided, e.g., by a micromanipulator, guides the adhesive body to above the sample; this may be effected either manually or automatically. Manual guiding is also possible. Sample selection may also be effected manually or automatically, provided that suitable image processing algorithms are available. The gripping tool with the adhesive body is then lowered on to the sample so that the at least partially curved surface of the adhesive body is brought into contact with the sample. When the gripping tool with the adhesive body is removed from the sample location, the sample adheres to the surface of the adhesive body. To facilitate the detachment of the sample from the surface of the sample location, it may be of advantage to cause the gripping tool to perform harmonic vibrations with an amplitude of a few micrometers, also known as microvibrations. Finally the sample is deposited at the depositing location. Depending on the kind of sample or the kind of analysis intended, the sample can be deposited with or without the adhesive body. If the sample is to be deposited with the adhesive body, advantageously the gripping tool can be made to perform one or several impact vibrations to facilitate deposition. The sample may be deposited, e.g., on to a biochip or on to a magnetic surface or into Eppendorf vessels.

Depositing can be performed with or without the adhesive body. Without deposition of the adhesive body, the sample—as a rule, a single cell—may, e.g., be stripped off onto a drop of a reaction liquid; if the surface of the reaction liquid, e.g., an aqueous solution, is curved more strongly, the adhesive forces of the liquid with respect to the cell will outperform the latter's adhesion to the adhesive body.

The movement of the gripping tool in the visual field of a microscope added to the apparatus can be adapted by suitable control means in such a way that the gripping tool moves at a speed that, for an observer, is always essentially the same, i.e. at a speed that is correspondingly lower at a high magnification than it is at a low magnification.

In a preferred embodiment of the method, the picking up of the sample is monitored in such a way that the gripping tool with the adhesive body and the sample is rotated and/or traversed and imaged into a camera. In this way the adhesive body with the sample, which is at the bottom side of the adhesive body where it is invisible to an observer, is made visible. Thus it is possible to exclude the risk that analysis vessels are only apparently filled in case sample pick-up fails. In prior art, the lack of this monitoring possibility frequently leads to faulty analyses, e.g., lacking augmentation reactions.

The picking up of the sample can also be documented in such a way that the gripping tool with adhesive body and sample is imaged into a camera via at least one mirror. In this way, rotation is unnecessary if the surface from which the sample is removed, the mirror and the camera are arranged at suitable locations relative to each other.

In a special embodiment of the method, the sample is fixed for the performance of some sample manipulation, especially microdissection, before it is removed by means of the adhesive body. This is preferable especially if a cell is to be released from a cell aggregate. Here, the gripping tool with the adhesive body is lowered onto the sample, which can then be fixed by exerting on it a correspondingly low force by the gripping tool via the adhesive body. The pressure or force may also be created by the micromanipulator. Once the sample is fixed, microdissection can be performed by means of another sample manipulator, e.g., a laser.

BRIEF DESCRIPTION OF THE DRAWINGS

Below, the invention is described in some detail on the basis of an exemplary embodiment with reference to the attached drawings, in which.

DETAILED DESCRIPTION

Figure 1:
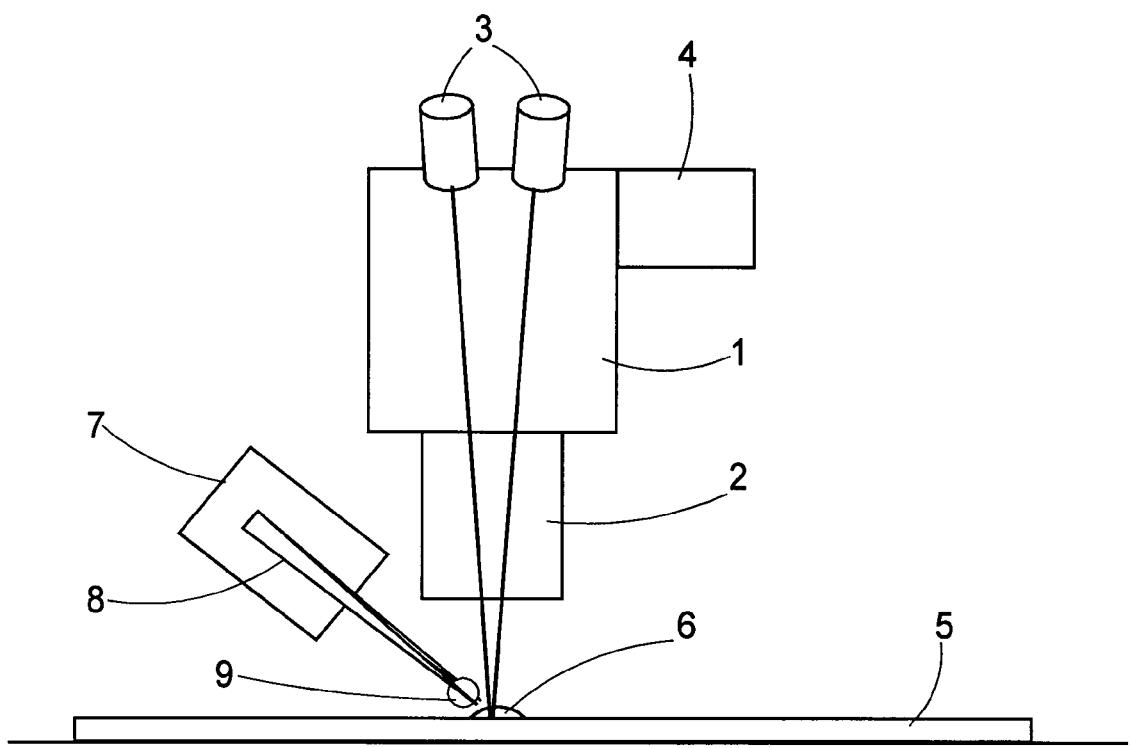
FIG. 1 is a sketch illustrating the principle of an arrangement according to the invention.

FIG. 1 shows an apparatus according to the invention with which the method according to the invention can be implemented. Suitably the apparatus comprises a stereomicroscope 1, with which, especially if the gripping tool is operated manually, the picking up of the sample can be observed three-dimensionally and carried out. Here, the commonly provided revolving nosepiece with objectives is symbolized by an objective 2. On the observer's side, the stereomicroscope 1 is provided with two eyepieces 3, with which an observer can observe the picking up of the sample and at least part of the transfer. The stereomicroscope 1 is further provided with a facility for switching the beam path so as to direct it onto a camera 4 instead of to the eyepieces 3. The beam path in the stereomicroscope is illustrated by the two black lines that start at the eyepieces 3 and meet on a sample carrier 5. On the sample carrier 5 there is a sample 6. Left of the stereomicroscope 1 there is a micromanipulator 7, which is movable within limits in all three spatial directions. The holder intended for it—preferably provided on the microscope body—is not shown. As a gripping tool, a pair of tweezers 8 is clamped into the micromanipulator 7. The legs of the tweezers 8 hold, at their tips, an adhesive body, which has the shape of a sphere 9 here. The sample carrier 5 may, e.g., be a specimen slide, but it may just as well be a piece of clothing.

The sample 6 may, e.g., be single cells. Moreover, the stereomicroscope 1 may be capable of fluorescence work; accordingly, the tweezers 8 and the sphere may be provided at least partially with a fluorescent layer. The sphere 9 is intended for picking up the cell and transporting it. Preferably, the sphere 9 is a microsphere of some plastic material, such as, e.g., polystyrene or some biopolymer. In other cases it may be preferable to use a glass sphere as adhesive body 9, as this is better for depositing the sample into a drop of water of appropriate surface curvature. The diameter of the sphere may be between 10 μm and 500 μm. Smaller and larger diameters are also possible and may even be preferable, depending on the size of the sample. The drawing does not show a reservoir for the spheres 9, from which a new sphere 9 is taken before every sample pick-up. For this purpose, it is useful if the reservoir is provided with a dispensing device. Alternatively, where contamination of the sample is not a consideration, the same sphere 9 may be used over and over again, although this will rather be exceptional.

Figure 2A:
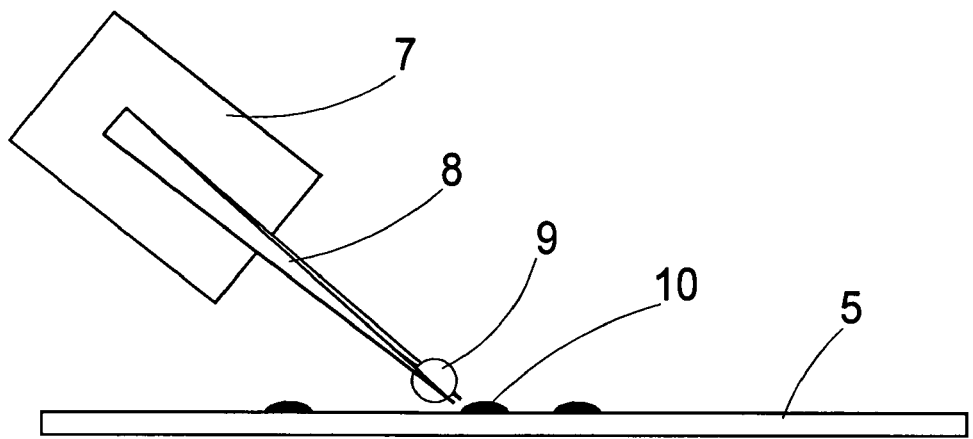
FIGS. 2a-c show the picking up of a sample.
Figure 2B:
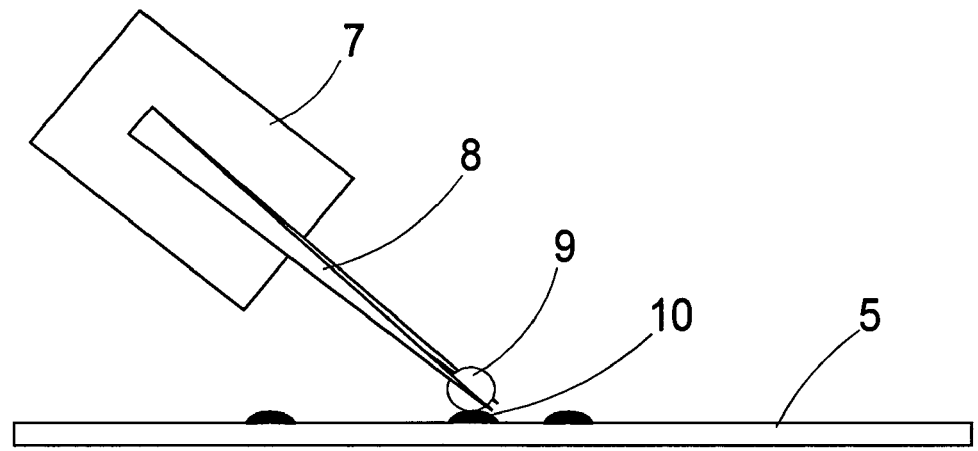
Figure 2C:
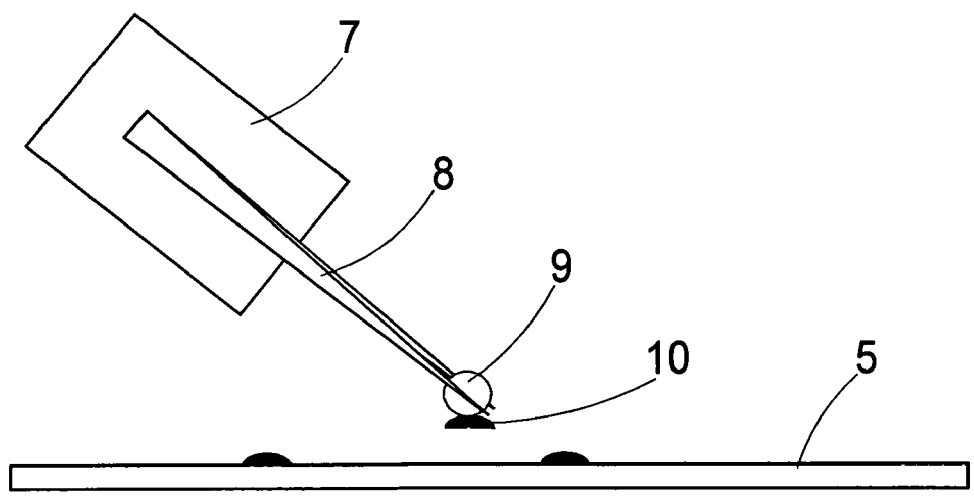

FIGS. 2a through 2c show the picking up of a sample, here, one of several cells, by means of the tweezers 8. First, a sphere 9 is taken from the dispenser by means of tweezers 8, which are guided by the micromanipulator 7, and moved towards the cell 10 to be isolated. This state is shown in FIG. 2a. FIG. 2b shows the sphere 9 making contact with the cell 10. Upon contacting the sphere 9, the cell 10 adheres to it. To facilitate the release of the cell from the sample carrier 5, the latter may be sprayed with a suitable liquid before, e.g., 50% ethanol. In addition, adhesion of the cell 10 to the sphere 9 may be helped by providing the sphere 9 at least partially with a very thin adhesive layer. The adhesive layer may be, e.g., some biosynthetically made polypeptide of non-animal origin or, alternatively, some cellulose derivative polymer. Suitable layers are such whose adhesive action is restricted to biological material, while not affecting the tweezers, for example. FIG. 2c shows the cell 10 adhering to the sphere 9 when this is removed with the tweezers 8.

Figure 3:
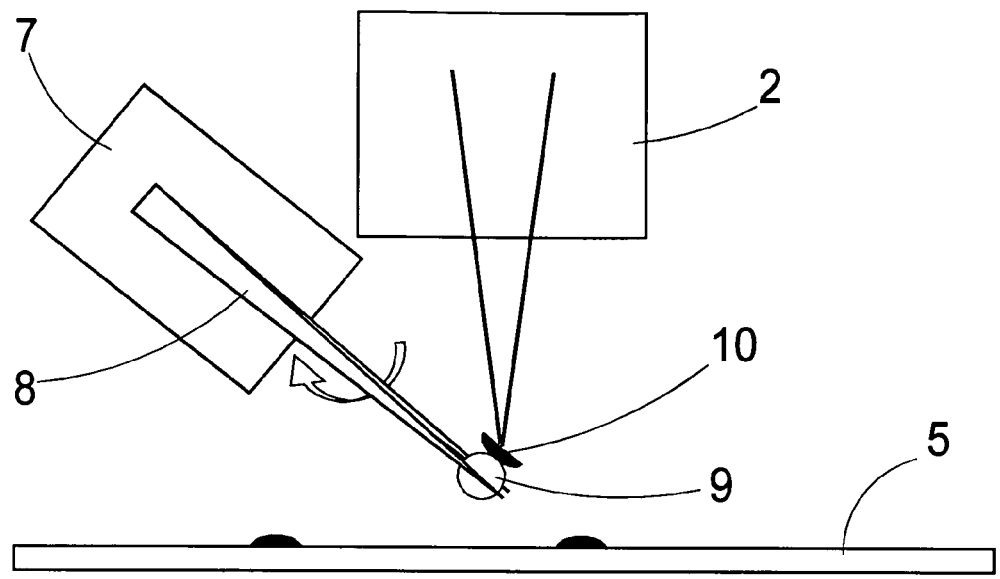
FIG. 3 shows the direct monitoring or documentation of picking up the sample.
Figure 4:
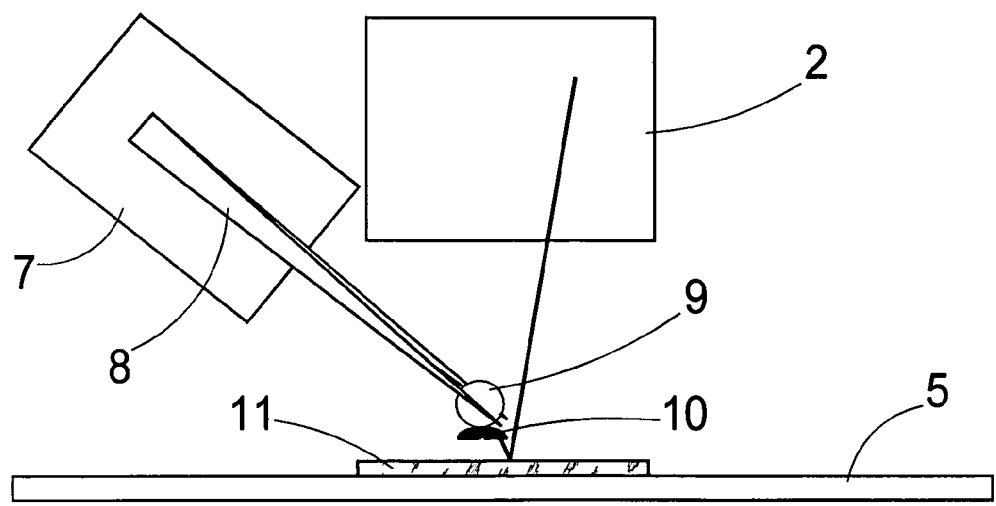
FIG. 4 shows an indirect monitoring of picking up the sample, and FIGS. 5a, b show the targeted depositing of the adhesive body with the sample at a depositing location intended therefor.

FIGS. 3 and 4 show how the picking up of the cell 10 is documented. For this purpose, e.g., the tweezers 8 may be rotated in the micromanipulator 7, or the micromanipulator 7 may be rotated as a whole about its longitudinal axis, as indicated by the arrow in FIG. 3. Now the cell 10 adhering to the sphere 9 is in the field of view of the objective 2 of the stereomicroscope 1. The image can be observed by an observer or imaged into a camera. An alternative possible if an upright microscope or stereomicroscope is used is shown in FIG. 4. Here, a mirror 11 is attached to the sample carrier 5. After the cell 10 has been picked up, the sample carrier 5 is traversed in the object plane until the mirror is in the image field of the microscope. The sample carrier 5 symbolizes all feasible kinds of working surfaces, e.g., a stage with a recess for transparent specimen slides on which the samples are arranged.

Figure 5A:
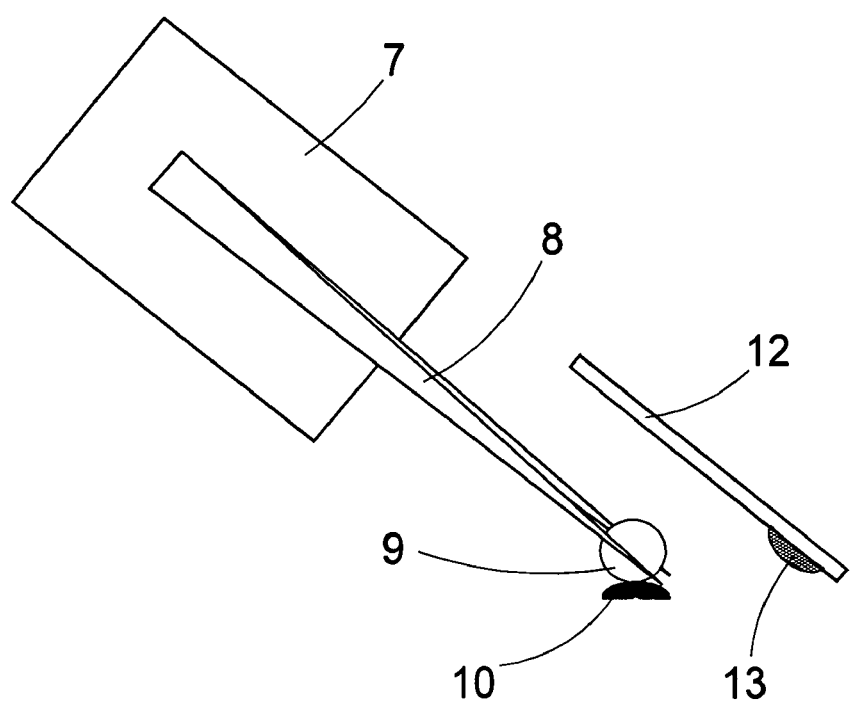
Figure 5B:
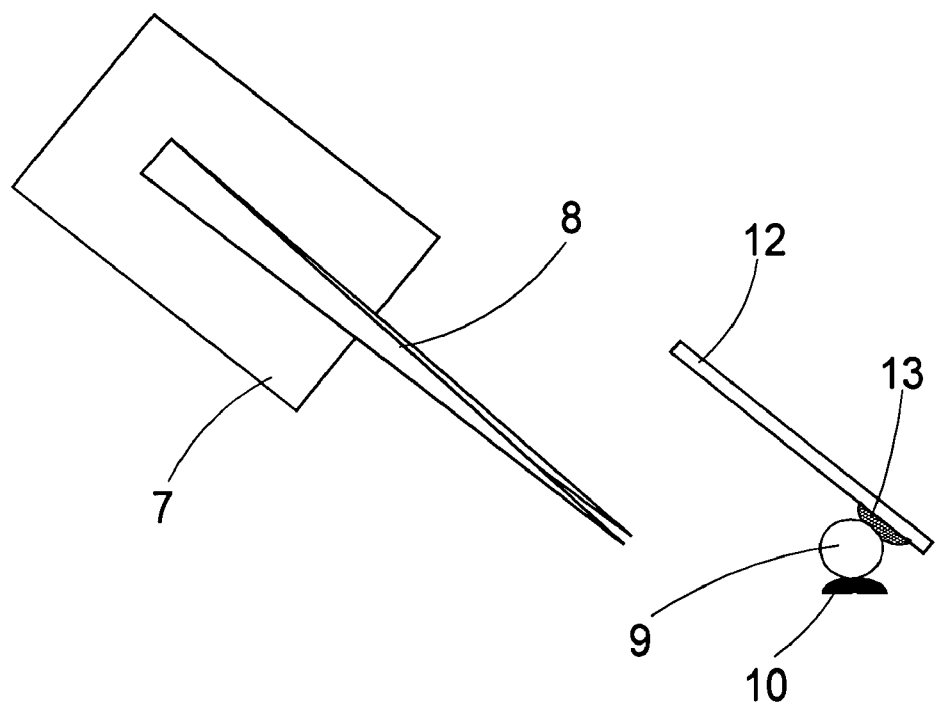

FIGS. 5a and 5b show how the sphere 9 with the cell 10 is moved to another sample carrier 12 and deposited there. Here, the sphere 9 is deposited together with the cell 10. This way of depositing is easier to implement than a deposition of the cell alone. Moreover, it ensures freedom from contamination. The cell can be deposited with pinpoint accuracy, e.g., on the bottom of an Eppendorf vessel, in a defined position of a transfer unit for subsequent mass-spectrometry, such as a MALDI plate (MALDI=matrix-assisted laser desorption and ionization), or on a defined spot of a biochip. The depositing location on the sample carrier 12 is preferably coated with a thin adhesive film 13, which may have, e.g., special curing properties, so that the depositing location may be coated with the adhesive film 13 weeks or months before its use. Alternatively, the sphere 9 may also be deposited onto a magnetized surface. For this purpose it is advantageous if the sphere also consists of some magnetic material or has a magnetic core at least. It is also possible to deposit the sphere 9, or the cell 10 without the sphere 9, into a drop of liquid.

With the apparatus invented, smallest objects can be isolated from preparations, picked up with pinpoint accuracy, transported to a depositing location and deposited there with pinpoint accuracy. The transfer is contamination-free and can be documented, which results in a great number of applications, e.g., in fundamental biological research and in forensic investigations.

| List of Reference Numbers |
| --- |
| 1 Stereomicroscope |
| 2 Objective |
| 3 Eyepieces |
| 4 Camera |
| 5 Sample carrier |
| 6 Sample |
| 7 Micromanipulator |
| 8 Tweezers |
| 9 Sphere |
| 10 Cell |
| 11 Mirror |
| 12 Sample carrier |
| 13 Adhesive film |

What is claimed is:

1. A method for transferring a microscopic sample from a sample location to a depositing location, comprising:
   picking up an adhesive body via a mechanical gripping tool wherein the adhesive body has an at least one outwardly-curved surface which is at least partially adhesive with respect to a microscopic sample;
   guiding the adhesive body to a position adjacent the microscopic sample with the mechanical gripping tool;
   bringing the at least one outwardly-curved surface of the adhesive body into contact with the microscopic sample, such that at least a portion of the microscopic sample adheres to the at least one outwardly-curved surface of the adhesive body when the adhesive body is moved away from an initial sample location; and
   depositing the microscopic sample at a depositing location.

2. The method as claimed in claim 1, further comprising depositing the adhesive body with the microscopic sample adhering thereto at the depositing location.

3. The method as claimed in claim 1, further comprising microvibrating the mechanical gripping tool when picking up the adhesive body.

4. The method as claimed in claim 1, further comprising subjecting the mechanical gripping tool to an impact when depositing.

5. The method as claimed in claim 1, further comprising:
   monitoring the bringing step;
   rotating and/or translating the mechanical gripping tool with the adhesive body; and
   imaging the microscopic sample via a camera.

6. The method as claimed in claim 1, further comprising documenting at least one of: the picking up of the adhesive body and the microscopic sample in such a way that at least one of the adhesive body and the microscopic sample is imaged into a camera via a mirror.

7. The method as claimed in claim 1, further comprising, securing the microscopic sample for the performance of a sample manipulation procedure prior to the depositing of the microscopic sample by adhesion to the adhesive body.

8. The method as claimed in claim 1, further comprising fixing the microscopic sample for a microdissection procedure prior to the bringing of the microscopic sample by adhesion to the adhesive body.

* * * * *